(12) United States Patent
Splinter et al.

(10) Patent No.: US 10,411,497 B2
(45) Date of Patent: Sep. 10, 2019

(54) POWER GENERATION FOR RADIATION SYSTEM

(71) Applicant: Analogic Corporation, Peabody, MA (US)

(72) Inventors: Patrick Splinter, Middleton, MA (US); Steven Weed, Marblehead, MA (US); Steven Urcuk, Melrose, MA (US)

(73) Assignee: Analogic Corporation, Peabody, MA (US)

( * ) Notice: Subject to any disclaimer, the term of this patent is extended or adjusted under 35 U.S.C. 154(b) by 391 days.

(21) Appl. No.: 15/103,937

(22) PCT Filed: Dec. 12, 2013

(86) PCT No.: PCT/US2013/074677
§ 371 (c)(1),
(2) Date: Jun. 13, 2016

(87) PCT Pub. No.: WO2015/088535
PCT Pub. Date: Jun. 18, 2015

(65) Prior Publication Data
US 2017/0025890 A1  Jan. 26, 2017

(51) Int. Cl.
*A61B 6/00* (2006.01)
*H02K 7/108* (2006.01)
(Continued)

(52) U.S. Cl.
CPC ............. *H02J 7/1415* (2013.01); *A61B 6/56* (2013.01); *H05G 1/10* (2013.01)

(58) Field of Classification Search
CPC .. H05G 1/10; A61B 6/482; A61B 6/56; A61B 6/504; A61B 6/481; A61B 6/4441;
(Continued)

(56) References Cited

U.S. PATENT DOCUMENTS 1,545,175 A    7/1925  Turbayne
4,200,797 A    4/1980  Bax
(Continued)

FOREIGN PATENT DOCUMENTS

EP    0011458 A1    5/1980
JP    H057581 A     1/1993
WO    2008017983 A2 2/2008

OTHER PUBLICATIONS

First Chinese Office Action cited in Chinese Application No. 201380081324.6 dated Dec. 12, 2017, 10 pgs.
(Continued)

*Primary Examiner* — Don K Wong
(74) *Attorney, Agent, or Firm* — TraskBritt (57) ABSTRACT

One or more techniques and/or systems are described for generating power on a rotating unit of a system, such as a radiation system (e.g., CT system). The rotating unit comprises a generator that comprises a drive wheel. The drive wheel interfaces with a drive mechanism of a stationary unit. As the rotating unit is moved relative to the stationary unit, the drive wheel rotates along the drive mechanism causing power to be generated by the generator. The power may be supplied to one or more electronic components of the rotating unit.

21 Claims, 7 Drawing Sheets

(51) Int. Cl.
*H02J 7/14* (2006.01)
*H05G 1/10* (2006.01)

(58) Field of Classification Search
CPC ....... A61B 6/4405; A61B 6/035; A61B 6/032;
A61B 2560/0214; A61B 2560/0219;
G01N 23/046; G01N 2223/419
See application file for complete search history.

(56) References Cited

U.S. PATENT DOCUMENTS

| | | |
|---|---|---|
| 4,663,536 A | 5/1987 | Roesel, Jr. et al. |
| 5,224,138 A | 6/1993 | Hirao et al. |
| 5,808,376 A | 9/1998 | Gordon et al. |
| 6,823,037 B2 | 11/2004 | Riemer et al. |
| 7,197,113 B1 | 3/2007 | Katcha et al. |
| 9,820,708 B2 * | 11/2017 | Risher-Kelly ....... A61B 6/4435 |
| 2001/0008552 A1 | 7/2001 | Harada et al. |
| 2010/0066340 A1 | 3/2010 | Delforge |
| 2010/0220837 A1 | 9/2010 | Bressel |
| 2011/0176654 A1 * | 7/2011 | Reichel |
| 2012/0256099 A1 * | 10/2012 | Gregerson ............. A61B 6/035 250/453.11 |
| 2014/0085042 A1 * | 3/2014 | Dobbs |

OTHER PUBLICATIONS

International Search Report cited in related application No. PCT/US13/74677 dated Jun. 26, 2014, pp. 14.
EP Communication cited in EP Application No. 13 815 324.2 dated Jan. 25, 2018, 7 pgs.
Second Chinese Office Action cited in Chinese Application No. 201380081324.6 dated Jun. 8, 2018, 5 pgs.
EP Communication cited in EP Application No. 13815324.2 dated May 22, 2017, 3 pgs.
Written Opinion of the International Searching Authority for PCT Application No. PCT/US2013/074677 dated Jun. 26, 2014, eight pages.
Chinese Office Action for Application No. 201380081324.6 dated Jun. 8, 2018, seven pages with translation.

* cited by examiner

POWER GENERATION FOR RADIATION SYSTEM

CROSS-REFERENCE TO RELATED APPLICATIONS

This application is a national phase entry under 35 U.S.C. § 371 of International Patent Application PCT/US2013/074677, filed Dec. 12, 2013, designating the United States of America and published in English as International Patent Publication WO 2015/088535 A1 on Jun. 18, 2015.

BACKGROUND

The present application relates to generating power for a radiation system using a generator situated on a rotating unit of the radiation system. The generator generates power based upon a rotational motion of the rotating unit relative to a stationary unit of the radiation system. While it finds particular application in the context of computed tomography (CT), it may also relate to other applications where it is desirable to deliver power to electronic components of a rotating unit.

Electronic components of a rotating unit often require power to be provided via a power coupling apparatus. For example, in CT systems, this power coupling apparatus typically comprises a slip-ring assembly and/or an inductive coupler configured to transfer power between a rotating unit and a stationary unit and/or between two rotating units.

Slip-ring assemblies are configured to transfer power between a rotating unit and another unit (e.g., a stationary unit or a second rotating unit) through the contact of two materials (e.g., via a sliding contact). Typically, these assemblies comprise two or more continuous conducting rings and two or more electrically conductive brushes. A first conducting ring is formed by the rotating unit and the second conducting ring is formed by the other unit. The brushes are coupled to at least one of the conducting rings, and during rotation of the rotating unit, the brushes that are coupled to a conducting ring rub against the other conducting ring to transfer power between the two units. While the use of slip-ring assemblies has proven effective for supplying power to electronic components of a rotating unit, slip-ring assemblies may be costly, may produce dust, and/or may require periodic maintenance.

Inductive couplers are configured to inductively transfer power between a rotating unit and another unit (e.g., a stationary unit or a second rotating unit). A primary winding is formed by a first unit, such as the stationary unit, and a secondary winding is formed by a second unit, such as the rotating unit. An alternating current is passed through the primary winding to induce a current in the secondary winding. In this way, power is transferred between the primary winding and the secondary winding, for example. While the use of inductive couplers has proven effective for supplying power to electronic components of a rotating unit, inductive couplers may be costly and/or require relatively high manufacturing precision.

BRIEF SUMMARY

Aspects of the present application address the above matters, and others. According to an aspect, a radiation system is provided. The radiation system comprises a stationary unit and a rotating unit configured for movement relative to the stationary unit. The rotating unit comprises a radiation source configured to generate radiation and a generator configured to generate power for an electronic component of the rotating unit.

According to an aspect, a method for generating power in a radiation system is provided. The method comprises moving a rotating unit of the radiation system relative to a stationary unit of the radiation system to derive a rotational motion. The method also comprises generating power via a generator based upon the rotational motion, the power supplied to an electronic component of the rotating unit.

According to an aspect, a radiation system is provided. The radiation system comprises a stationary unit, which comprises a drive mechanism. The radiation system also comprises a rotating unit configured for rotational motion relative to the stationary unit. The rotating unit comprises a radiation source configured to generate radiation and a detector array configured to detect at least some of the radiation. The rotating unit also comprises a generator configured to generate power based upon the rotational motion, the generator comprising a drive wheel configured for rotation along the drive mechanism.

Those of ordinary skill in the art will appreciate still other aspects of the present application upon reading and understanding the appended description.

BRIEF DESCRIPTION OF THE DRAWINGS

The application is illustrated by way of example and not limitation in the figures of the accompanying drawings, in which like references indicate similar elements and in which.

DETAILED DESCRIPTION

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

The present disclosure relates to an apparatus for generating power within a rotating unit of a system, such as a computed tomography (CT) system. The rotating unit comprises a generator configured to generate the power, which is supplied to one or more electronic components of the rotating unit. By way of example, the generator may be configured to supply power to a radiation source, detector array, cooling component, and/or communication component of the rotating unit.

According to some embodiments, a stationary unit of the system includes a drive mechanism along which a drive wheel of the generator rotates. By way of example, during operation of the system, the rotating unit may be rotated relative to the stationary unit (e.g., including the drive mechanism) to derive a rotational motion. This rotational motion may cause the drive wheel to rotate along the drive mechanism, causing a shaft of the generator to rotate. The rotation of the shaft may, in-turn, create an electrical field that facilitates the generation of power by the generator. The power is subsequently supplied to one or more electronic components of the rotating unit. In this way, power that is supplied to one or more electronic components of the rotating unit is generated within the rotating unit as opposed to being transferred to the rotating unit via a slip-ring assembly and/or inductive coupler, for example. In other examples, the power generated by the generator is supplemented with power transferred to the rotating unit via a slip-ring assembly, inductive coupler, and/or other auxiliary power supply.

Figure 1:
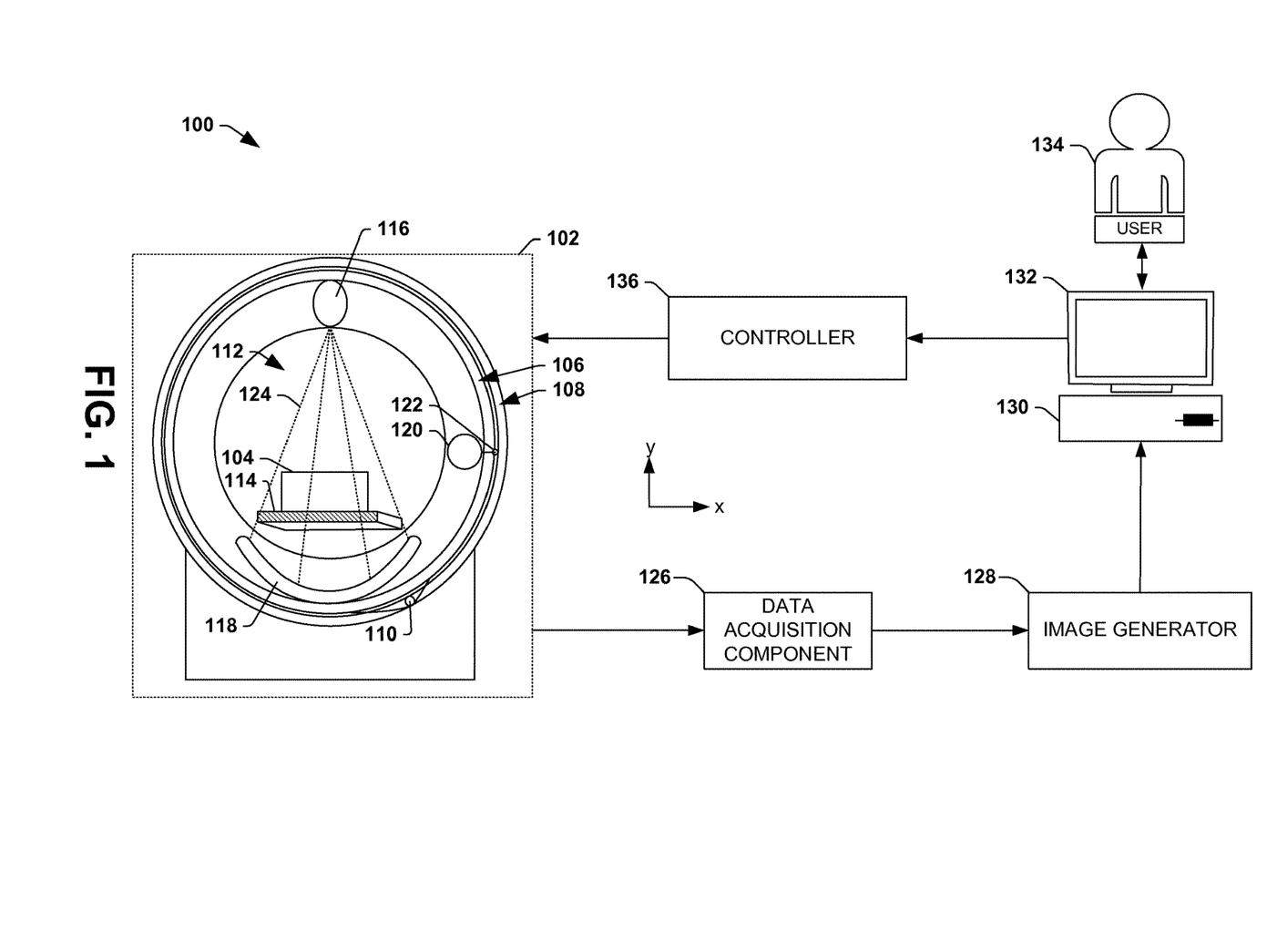
FIG. 1 is a schematic block diagram illustrating an example computed tomography (CT) system.

FIG. 1 illustrates a CT system 100 comprising a power apparatus according to some embodiments. It is to be appreciated that while a CT system 100 is described herein, the instant application is not intended to be so limited. That is, to the extent practical, the instant application, including the scope of the claimed subject matter, is intended to be applicable to other systems that comprise a rotating unit having one or more electronic components and configured for movement relative to a unit, such as a stationary unit and/or a second rotating unit (e.g., which moves at a different speed and/or in a different direction than the rotating unit).

Moreover, it is to be appreciated that the example arrangement is not intended to be interpreted in a limiting manner, such as necessarily specifying the location, inclusion, and/or relative position of the components depicted therein. By way of example, in some embodiments, a data acquisition component 126 is part of a detector array 118.

An examination unit 102 of the CT system 100 is configured to examine objects 104 such as baggage, cargo, patients, etc. (e.g., where a cross-sectional view of the examination unit 102 is illustrated in FIG. 1). The examination unit 102 comprises a rotating unit 106 configured to rotate relative to a stationary unit 108 in a rotational motion (e.g., rotating clockwise or counter-clockwise on the page) via a rotator 110 of the stationary unit 108, for example. By way of example, the rotator 110 may comprise a belt, chain, or gear-system configured to drive the rotating unit 106, causing the rotating unit 106 to be rotated relative to the stationary unit 108. It is to be appreciated that while the instant application describes the rotating unit 106 as rotating relative to a stationary unit 108, in other embodiments, the rotational motion of the rotating unit 106 may be described relative to a second rotating unit that rotates in a different direction and/or at a different rotational speed, for example.

A bore 112, formed by the rotating unit 106, defines a parameter of an examination region in which objects 104 are examined. Objects 104 are translated through the examination region via a support article 114, such as a bed, conveyor belt, or roller system, for example.

The rotating unit 106 comprises a radiation source 116 (e.g., an ionizing radiation source such as an x-ray source or gamma-ray source) and a detector array 118. In some embodiments, the detector array 118 and radiation source 116 are positioned on diametrically opposing portions of the rotating unit 106 relative to the bore 112. For example, in the illustrated embodiment, the radiation source 116 is positioned above the bore 112 and the detector array 118 is positioned below the bore. It is to be appreciated that because the radiation source 116 and the detector array 118 are mounted to the rotating unit 106, a relative position between the radiation source 116 and the detector array 118 is substantially maintained during the rotational motion of the rotating unit 106. In some embodiments, the rotation of the radiation source 116 and detector array 118 (e.g., within an x, y plane) in tandem with the translation of an object 104 (e.g., in a direction perpendicular to the x, y plane (e.g., sometimes referred to as the z-direction)) causes a helical examination to be performed on the object 104. In other embodiments, the object 104 is not translated during the examination, and thus a helical examination is not performed despite the rotational motion of the rotating unit 106, radiation source 116, and detector array 118.

As will be further described in more detail below, the rotating unit 106 also comprises a generator 120 configured to generate power using the rotational motion of the rotating unit 106. For example, the generator 120 comprises a drive wheel 122 configured to glide or rotate along a drive mechanism (e.g., a guide) of the stationary unit 108 while the rotating unit 106 is rotated. The drive wheel 122 drives (e.g., spins) a shaft of the generator 120, which causes an electrical field to be generated within the generator 120 and/or cause power (e.g., electricity, etc.) to be produced by the generator 120. In this way, the rotational motion of the rotating unit 106 is utilized by the generator 120 to generate power, for example.

The generator 120 is electrically coupled to one or more electronic components of the rotating unit 106, such as the radiation source 116, the detector array 118, a cooling component, a communication component, battery, etc. and is configured to, at times, supply power to the one or more electronic components. In this way, at least some of the power supplied to one or more electronic components of the rotating unit 106 is generated using the rotational motion of the rotating unit 106.

During an examination of an object 104, the radiation source 116 emits cone-beam and/or fan-beam shaped radiation 124 from a focal spot of the radiation source 116 (e.g., a region within the radiation source 116 from which radiation 124 emanates) into the examination region. Such radiation 124 may be emitted substantially continuously and/or may be emitted intermittently (e.g., a brief pulse of radiation 124 is emitted followed by a resting period during which the radiation source 116 is not activated). Further, the radiation 124 may be emitted at a single energy spectra or multi-energy spectrums depending upon, among other things, whether the CT system is configured as a single-energy CT system or a multi-energy (e.g., dual-energy) CT system.

As the emitted radiation 124 traverses the object 104, the radiation 124 may be attenuated differently by different aspects of the object 104. Because different aspects attenuate different percentages of the radiation 124, the number of photons detected by respective detector cells of the detector array 118 may vary. For example, more dense aspects of the object(s) 104, such as a bone or metal plate, may attenuate more of the radiation 124 (e.g., causing fewer photons to impinge a region of the detector array 118 shadowed by the more dense aspects) than less dense aspects, such as skin or clothing.

Radiation detected by the detector array 118 may be directly or indirectly converted into analog signals that can be transmitted from the detector array 118 to a data acquisition component 126 operably coupled to the detector array 118. The analog signal(s) may carry information indicative of the radiation detected by the detector array 118. The information that can be derived from the analog signal may be a function of whether the detector array 118 is an integrating-type detector array (e.g., configured to integrate charge over a sampling period) and/or a photon counting type detector array (e.g., configured to count detection events and/or determine the energy of respective radiation photons).

The data acquisition component 126 is configured to convert the analog signals output by the detector array 118 into digital signals and/or to compile signals that were transmitted within a predetermined time interval, or measurement interval, using various techniques (e.g., integration, photon counting, etc.). The compiled signals are typically in projection space and are, at times, referred to as projections.

The projections and/or digital signals generated by the data acquisition component 126 may be transmitted to an image generator 128 (e.g., as times referred to as an image reconstructor) configured to convert the data from projection space to image space using suitable analytical, iterative, and/or other reconstruction techniques (e.g., tomosynthesis reconstruction, back-projection, iterative reconstruction, etc.). Such images may depict a two dimensional representation of the object 104 and/or a three dimensional representation of the object 104, for example. In other embodiments, the projections and/or digital signals may be transmitted to other processing components, such as a threat analysis component, for processing.

The example CT system also includes a terminal 130, or workstation (e.g., a computer), configured to receive image (s) from the image generator 128, which can be displayed on a monitor 132 to a user 134 (e.g., security personnel, medical personnel, etc.). In this way, the user 134 can inspect the image(s) to identify areas of interest within the object(s) 104. The terminal 130 can also be configured to receive user input, which can direct operations of the examination unit 102 (e.g., a speed of rotation, an energy level of the radiation 124, a desired voltage applied to the radiation source 116, etc.).

In the example CT system 100, a controller 136 is operably coupled to the terminal 130. The controller 136 may be configured to control operations of the examination unit 102, for example. By way of example, in some embodiments, the controller 136 may be configured to receive information from the terminal 130 and to issue instructions to the examination unit 102 indicative of the received information (e.g., adjust a speed of a conveyor belt, adjust a voltage applied to the radiation source 116, adjust a power characteristic, such as voltage characteristic and/or frequency characteristic, of power output by the generator 120 (e.g., such as through an instruction to adjust a gear ratio of gears within the generator 120), etc.).

Figure 2:
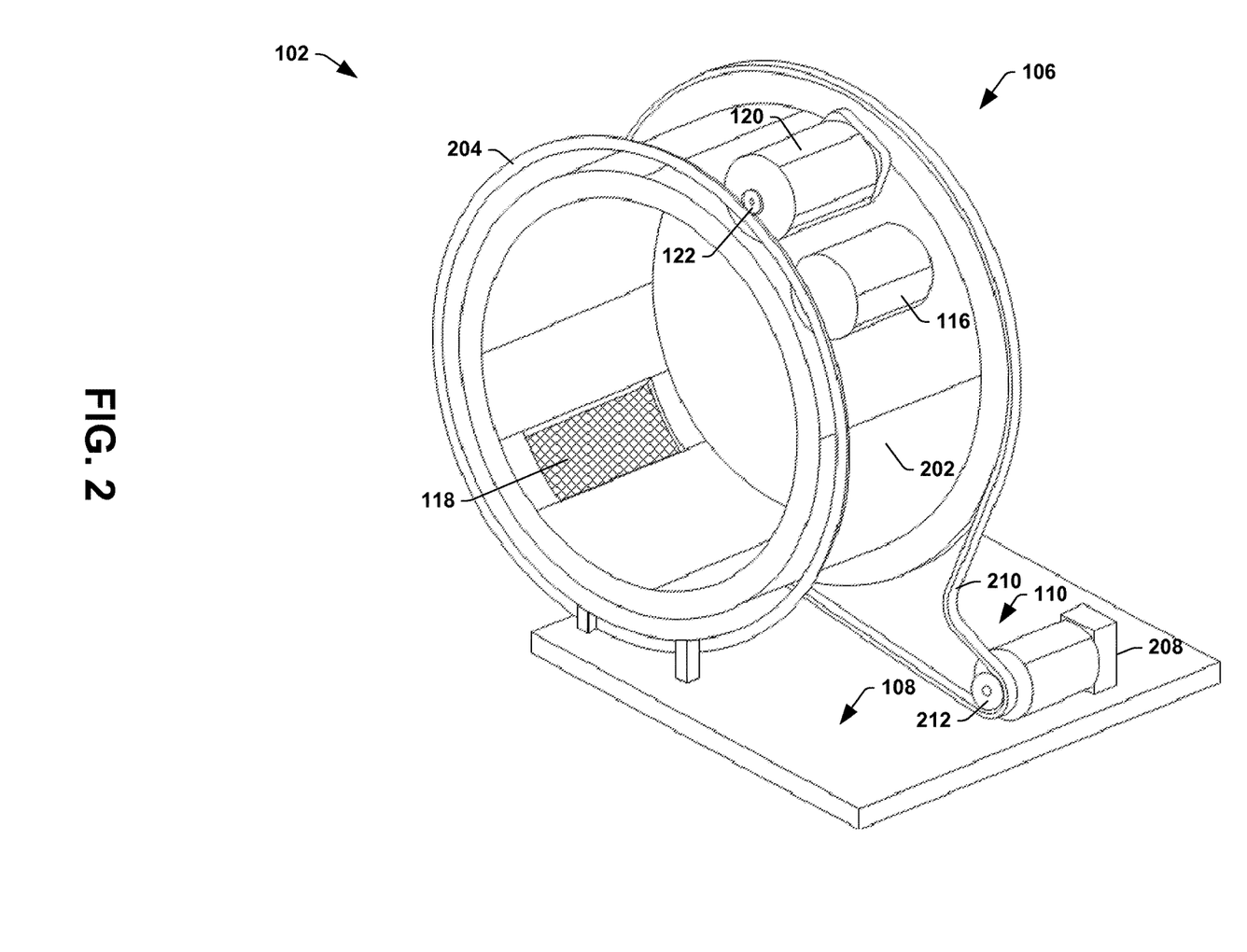
FIG. 2 illustrates a perspective view of an example examination unit of a CT system.

Referring to FIG. 2, a perspective view of an example examination unit 102 according to some embodiments is provided. The examination unit 102 comprises a rotating unit 106 and a stationary unit 108. The rotating unit 106 includes a rotating drum 202 to which the radiation source 116, the detector array 118, and the generator 120 are mounted. The stationary unit 108 includes the rotator 110 for rotating the rotating unit 106 and a drive mechanism 204 along which a drive wheel 122 of the generator 120 rotates during rotations of the rotating unit 106. It is to be appreciated that while the rotating unit 106 of the example examination unit 102 comprises a rotating drum 202, in other embodiments, the rotating drum 202 may be substituted with a substantially disk-shaped structure to which the radiation source 116, the detector array 118, and/or the generator 120 are mounted. It is also to be appreciated that although not illustrated, the rotating unit 106 is generally supported by one or more ball-bearings or other support elements (e.g., roller devices) which suspend the rotating unit 106 and/or facilitate rotation of the rotating unit 106.

The rotator 110 comprises a drive motor 208 and a belt 210, which interfaces with the rotating unit 106 and, at times, exerts a force on the rotating unit 106 that causes a rotational motion of the rotating unit 106. By way of example, the drive motor 208 comprises a pulley 212, which interfaces with the belt 210. When a command is received to rotate the rotating unit 106, the drive motor 208 engages the pulley 212, causing the pulley 212 to rotate relative to the drive motor 208. The rotation of the pulley 212 exerts a force on the belt 210 that causes the belt 210 to move, which, in turn, causes the rotating unit 106 to rotate.

It is to be appreciated that while reference is made herein to a drive motor 208, a belt 210, and a pulley 212, other interfacing elements configured to exert a force on the rotating unit 106 that causes the rotating unit 106 to rotate are also contemplated. By way of example, the belt 210 may be substituted with a chain or other semi-rigid structure configured to surround a portion of the rotating unit 106 and/or exert a force that causes the rotating unit 106 to rotate. As another example, the pulley 212 and the belt 210 may be substituted with a gear system, wherein teeth of the gear system engage teeth of the rotating drum 202 to exert a force that causes the rotating unit 106 to rotate. As still another example, the drive motor 208 may engage a roller that exerts such a force.

During a rotation of the rotating unit 106, the drive wheel 122 of the generator 120 engages a drive mechanism 204 of the stationary unit 108, such as a track, a belt, etc. and/or rotates along the drive mechanism 204. Accordingly, the rotation of the rotating unit 106 drives the drive wheel 122 along the drive mechanism 204. The drive wheel 122 of the generator 120 is coupled to a shaft of the generator 120, which is rotated due to the rotation of the drive wheel 122 along the drive mechanism 204. Such rotation of the shaft creates an electrical field within the generator 120 that causes power (e.g., electricity, etc.) to be generated by the generator 120, which is supplied (e.g., fed) to one or more electronic components of the rotating unit 106, such as the radiation source 116 and/or the detector array 118, for example. In some embodiments, a diameter of the drive mechanism 204 is selected to facilitate substantially continuous contact between the drive wheel 122 and the drive mechanism 204.

The drive wheel 122 may comprise a gear (e.g., comprising teeth that interface with teeth of the drive mechanism 204), a friction wheel, a pulley, and/or other interfacing element depending upon, among other things, the desired material and/or construction of the drive mechanism 204, for example. In some embodiments, a diameter of the drive wheel 122 and/or other characteristics of the drive wheel 122 are selected according to desired power characteristics of the power output by the generator 120. By way of example, the diameter of the drive wheel 122 may be selected based upon a desired frequency of the power.

Figure 3:
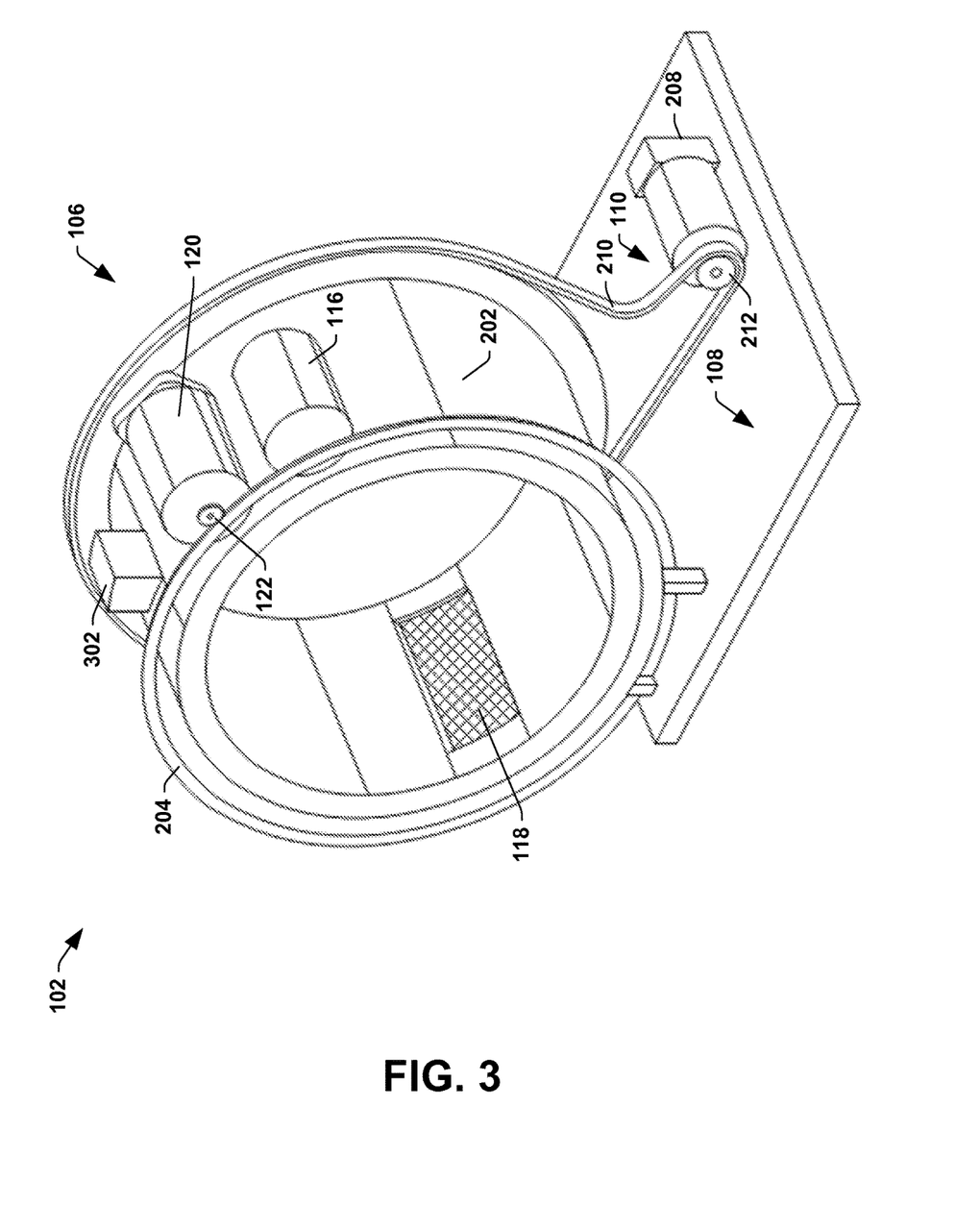
FIG. 3 illustrates a perspective view of an example examination unit of a CT system.

It is to be appreciated that because the generator 120 is configured to generate power based upon the rotational motion of the rotating unit 106, in some embodiments, little to no power may be generated by the generator 120 during periods when the rotating unit is not rotating (e.g., such as may occur when the CT system is idle and/or not examining objects). Accordingly, in applications where it is desirable to provide power to electronic components of the rotating unit 106 during periods when the rotating unit 106 is not rotating, an auxiliary power supply may be utilized by the examination unit 102 to provide such power. Referring to FIG. 3, a perspective view of an example examination unit 102 comprising an auxiliary power supply according to some embodiments is provided.

In this example, the rotating unit 106 comprises an energy storage component 302 (e.g., battery, capacitor, etc.) that is mounted to the rotating drum 202. The energy storage component 302 is configured to, at times, store power and to, at times, provide stored power to one or more electronic components of the rotating unit 106. By way of example, the energy storage component 302 may be configured to provide power to a communications component and/or a cooling component of the rotating unit 106 during periods when the rotating unit 106 is not rotating and/or when the generator 120 is not generating a sufficient amount of power for the communications component and/or the cooling component.

In some embodiments, the generator 120 is configured to charge the energy storage component 302 (e.g., feed power to the energy storage component 302) during periods when the generator 120 is generating power. In other embodiments, the energy storage component 302 is charged via other techniques. By way of example, power provided via a slip-ring assembly and/or an inductive coupler may be used to charge the energy storage component 302.

It is to be appreciated that the use of an energy storage component 302 is merely one technique for supplying power to one or more electronic components of the rotating unit 106 during periods when the generator 120 is not generating power and that other techniques are contemplated. By way of example, when the rotating unit 106 is not rotating, a power cable may be coupled to a power receptor of the rotating unit 106 and may supply power to one or more electronic components of the rotating unit 106. As another example, a slip-ring assembly and/or an inductive coupler may be used to, at times, supply power to one or more electronic components of the rotating unit 106.

It will be appreciated that while the foregoing techniques are described for supplying power to the rotating unit 106 at times when the rotating unit 106 is not rotating and/or the generator 120 is not generating power, at least some of the techniques may also be used to supplement power generated by the generator 120. By way of example, the energy storage component 302 may be configured to, at times, release stored power concurrently with the generator 120 generating power (e.g., such as at peak loads) to reduce the load on the generator 120. As another example, a slip-ring assembly and/or an inductive coupler may be configured to supply power to a first set of one or more electronic components of the rotating unit 106 concurrently with the generator 120 supplying power to a second set of one or more electronic components of the rotating unit 106 (e.g., where the first set and the second set may be a same set or different sets).

In still other embodiments, the examination unit 102 may be configured such that the generator 120 can generate power during periods when the rotating unit 106 is not rotating. By way of example, referring to FIG. 4, an example examination unit 102 according to some embodiments is provided. In such embodiments, the drive mechanism of the stationary unit comprises a second drive motor 402, a guide 404, and a second drive wheel 406. The second drive wheel 406 interfaces with the guide 404 to, at times, rotate the guide 404. By way of example, during periods when the rotating unit 106 is not rotating, the second drive motor 402 may be activated to rotate the second drive wheel 406, which in turn rotates the guide 404. In such embodiments, the guide 404 may be mounted to the stationary unit 108 via a ball-bearing apparatus or other apparatus configured to support the guide 404 and/or facilitate rotation of the guide 404 relative to the second drive motor 402.

Figure 4:
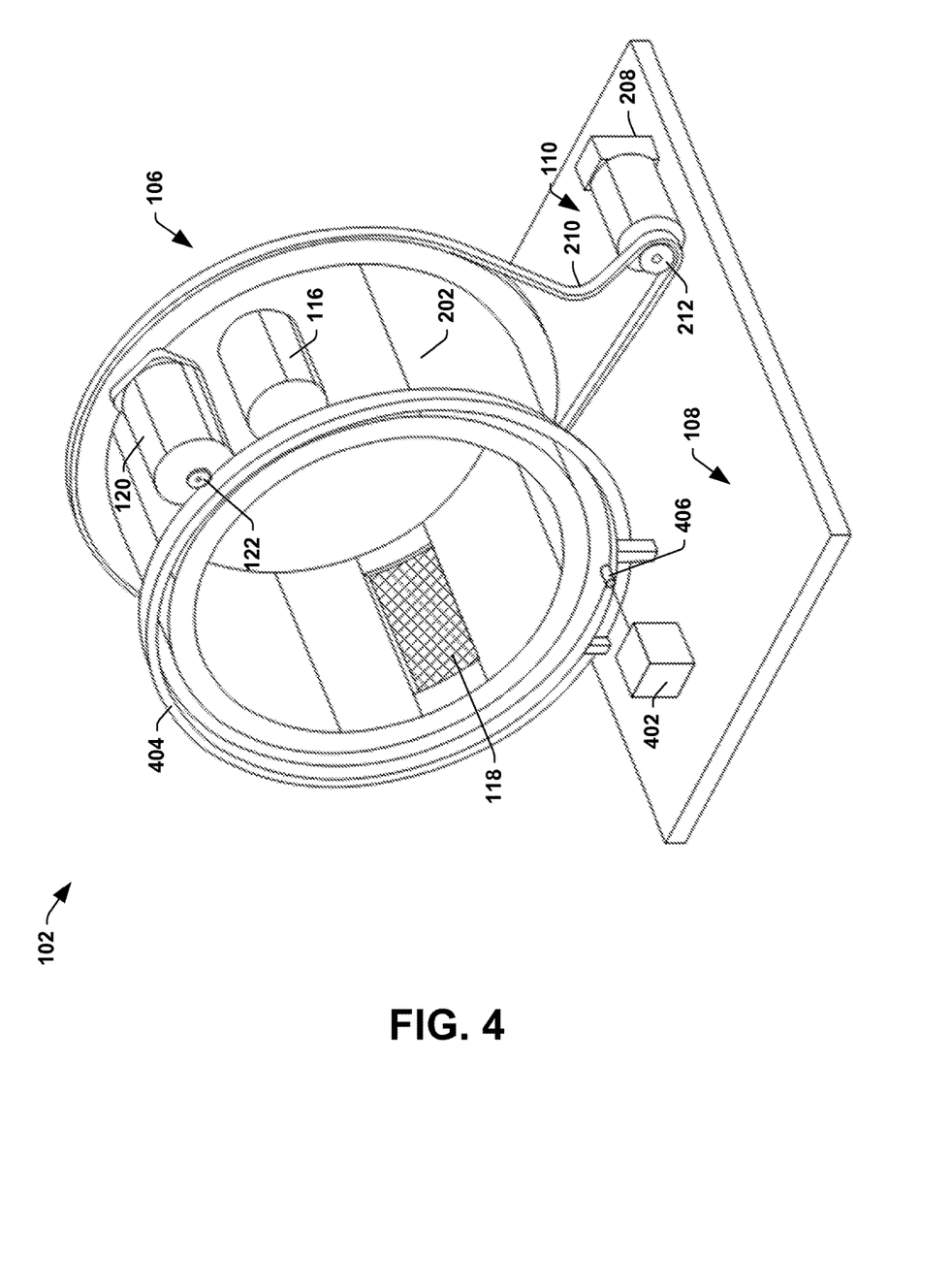
FIG. 4 illustrates a perspective view of an example examination unit of a CT system.

The drive wheel 122 of the generator 120 interfaces with the guide 404 and is configured to rotate along the guide 404 (e.g., or be rotated by the guide 404) as the guide 404 is rotated by the second drive wheel 406. Accordingly, the rotation of the guide 404 relative to the rotating unit 106 may facilitate the generation of power by the generator 120 during periods when the rotating unit 106 is not rotating.

In still other embodiments, a combination of the rotational motion of the rotating unit 106 and a rotational motion of the guide 404 may facilitate the generation of power by the generator 120. By way of example, the rotational speed of the rotating unit 106 may be a function of a desired imaging parameter (e.g., where power generation is merely a secondary consideration for the rotational speed). Where the rotational speed of the rotating unit 106 is faster than desired for power generation, the guide 404 may be rotated in a same direction as the rotating unit 106 (e.g., causing a relative rotational speed between the rotating unit 106 and the guide 404 to be less than a rotational speed of the rotating unit 106 relative to a stationary element) to reduce the rotational speed of the drive wheel 122 (e.g., where one or more power characteristics, such as frequency of the generated power, may be a function of the rotational speed of the drive wheel 122). Where the rotational speed of the rotating unit 106 is slower than desired for power generation, the guide 404 may be rotated in a direction opposite that of the rotating unit 106 (e.g., causing a relative rotational speed between the rotating unit 106 and the guide 404 to be more than a rotational speed of the rotating unit 106 relative to a stationary element) to increase the rotational speed of the drive wheel 122. Accordingly, in some embodiments, the drive mechanism of the stationary unit 108 may be used to control a rotational speed of the drive wheel 122 of the generator 120.

It is to be appreciated that the construction of the second drive wheel 406 and/or materials used for the second drive wheel 406 may vary based upon application and/or based upon the material and/or construction of the guide 404. By way of example, the second drive wheel 406 may be a gear, friction wheel, and/or pulley. Moreover, the guide 404 may be constructed of a rigid or semi-rigid material such as metal, plastic, rubber, etc., for example.

Figure 5:
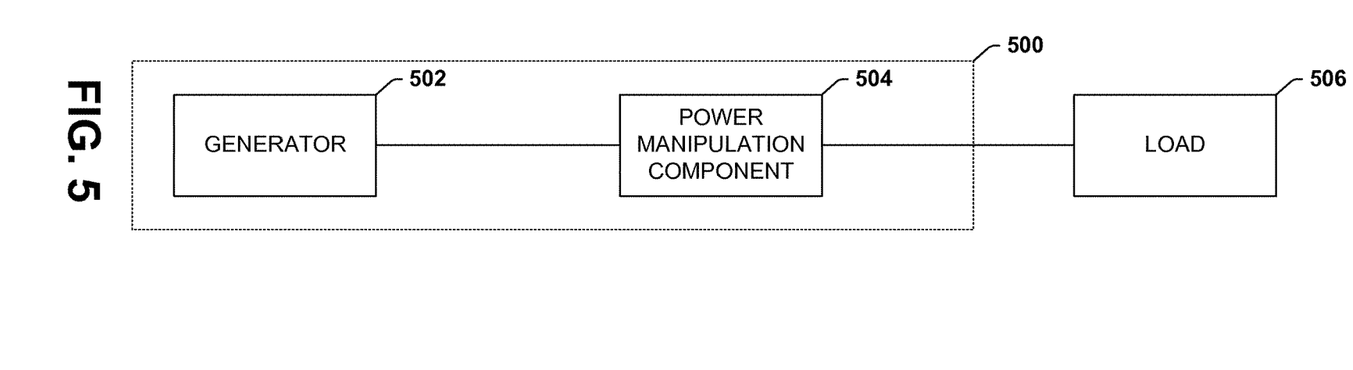
FIG. 5 illustrates a power apparatus of an example rotating unit.

Referring to FIG. 5, a component block diagram of a power apparatus 500 of a rotating unit 106 according to some embodiments is provided. The power apparatus 500 is configured to provide power to a load 506 (e.g., radiation source 116, detector array 118, communications component, cooling component, and/or other electronic component(s) of the rotating unit 106). The power apparatus 500 comprises a generator 502 (e.g., 120 in FIGS. 1-4) and a power manipulation component 504.

As described with respect to previous figures, the generator 502 is configured to generate power using the rotational motion of the rotating unit 106 and/or the rotational motion of a guide 404 of the stationary unit 108. Power characteristics of the power that is output by the generator 502 may be a function of, among other things, the rotational speed of the rotating unit 106, a relative rotational speed between the rotating unit 106 and the guide 404, a diameter of a drive wheel 122 of the generator 502, and/or a configuration of the generator 502. By way of example, in some embodiments, the generator 502 comprises a gear box that allows the operator and/or a controller, for example, to adjust a gear ratio of the generator 502 (e.g., to facilitate adjusting a frequency of the power that is output by the generator 502 and/or other power characteristic of the output), for example.

The power manipulation component 504 is configured to manipulate one or more power characteristics of the power that is output by the generator 502 based upon power requirements of the load 506. By way of example, the power manipulation component 504 may comprise a transformer configured to step-up or step-down a voltage applied to the load 506 by the generator 502 based upon voltage requirements of the load 506. As another example, the power manipulation component 504 may comprise a rectifier configured to convert alternating current generated by the generator 502 into direct current for delivery to the load 506.

It is to be appreciated that while the power apparatus 500 provides for merely a single power manipulation component 504, in some embodiments the power apparatus 500 may comprise a plurality of power manipulation components. By way of example, the detector array 118 of the rotating unit 106 may be configured to receive 120-volt electricity and the radiation source 116 of the rotating unit 106 may be configured to receive 480-volt electricity. Accordingly, a first power manipulation component may be coupled to the detector array 118 and may be configured to adjust a voltage applied to the detector array 118 by the generator 502 according to voltage requirements of the detector array 118 and a second power manipulation component maybe coupled to the radiation source 116 and may be configured to adjust a voltage applied to the radiation source 116 by the generator 502 according to voltage requirements of the radiation source 116. In still other embodiments, the power apparatus 500 may comprise a plurality of generators (e.g., mounted to the rotating unit 106), where a first generator is configured to generate power for the radiation source 116 (e.g., and/or one or more other components) and a second generator is configured to generate power for the detector array 118 (e.g., and/or one or more other components), for example.

In some embodiments, it is desirable to intermittently reduce energy consumption by one or more electronic components that are receiving power from the generator 502 (e.g., thus reducing a load on the generator 502). By way of example, it may be desirable to shut down the radiation source 116 (e.g., to reduce radiation emissions) when an object 104 is not being examined. Accordingly, a load on the generator 502 may fluctuate depending upon power consumption of the load 506. When the load on the generator 502 is reduced, the drive wheel 122 of the generator 502 may impose friction on the drive mechanism 204 or guide 404 (e.g., causing the rotational speed of the rotating unit 106 to be reduced unless such frictional force is compensated for, such as by the drive motor 208).

Figure 6:
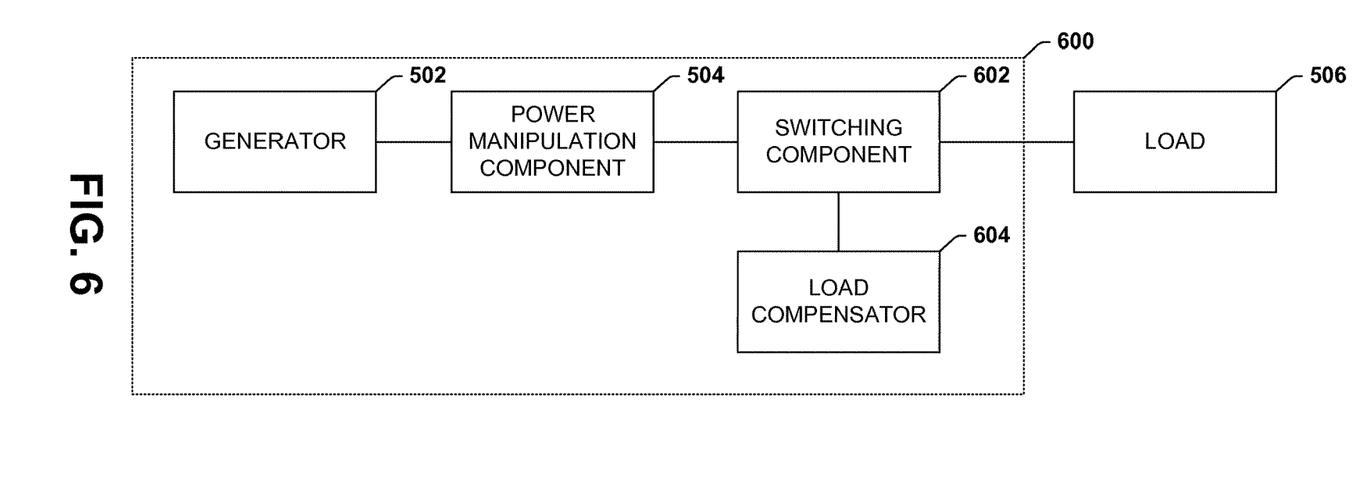
FIG. 6 illustrates a power apparatus of an example rotating unit.

FIG. 6 illustrates a component block diagram of an example power apparatus 600 configured to compensate for a reduction in energy consumption by one or more electronic components of the rotating unit 106 (e.g., to reduce or minimize the imposition of friction on at least one of the drive mechanism 204 or guide 404). More particularly, the power apparatus 600 additionally comprises a switching component 602 and a load compensator 604 (e.g., a resistor configured to convert the power into heat). The switching component 602 is configured to switch the load on the generator 502 between the load 506 and the load compensator 604 based upon energy consumption of the load 506. By way of example, at times when it is desirable to turn-off the radiation source 116 (e.g., the load 506), the switching component 602 may electrically decouple the load 506, or a portion thereof, from the generator 502 and electrically couple the load compensator 604 to the generator 502. In this way, the load compensator 604 compensates for a change in the load placed on the generator 502 by the electronic component(s) such that the generator 502 experiences little to no change in the load when the radiation source 116 is switched off, for example. Moreover, due to the electrical load on the generator 502 being held substantially constant (e.g., due to the load compensator 604 compensating for a reduction in power drawn by the load 506), little to no friction may be imposed on the drive mechanism 204 and/or guide 404 due to the reduction in power drawn by the load 506 (e.g., and thus the drive motor 208 may experience little to no change in mechanical load due to the reduction in power drawn by the load 506), for example.

It is to be appreciated that while FIG. 6 illustrates the switching component 602 as being electrically situated between the power manipulation component 504 and the load 506, in other embodiments, the switching component 602 is electrically situated between the generator 502 and the power manipulation component 504.

Figure 7:
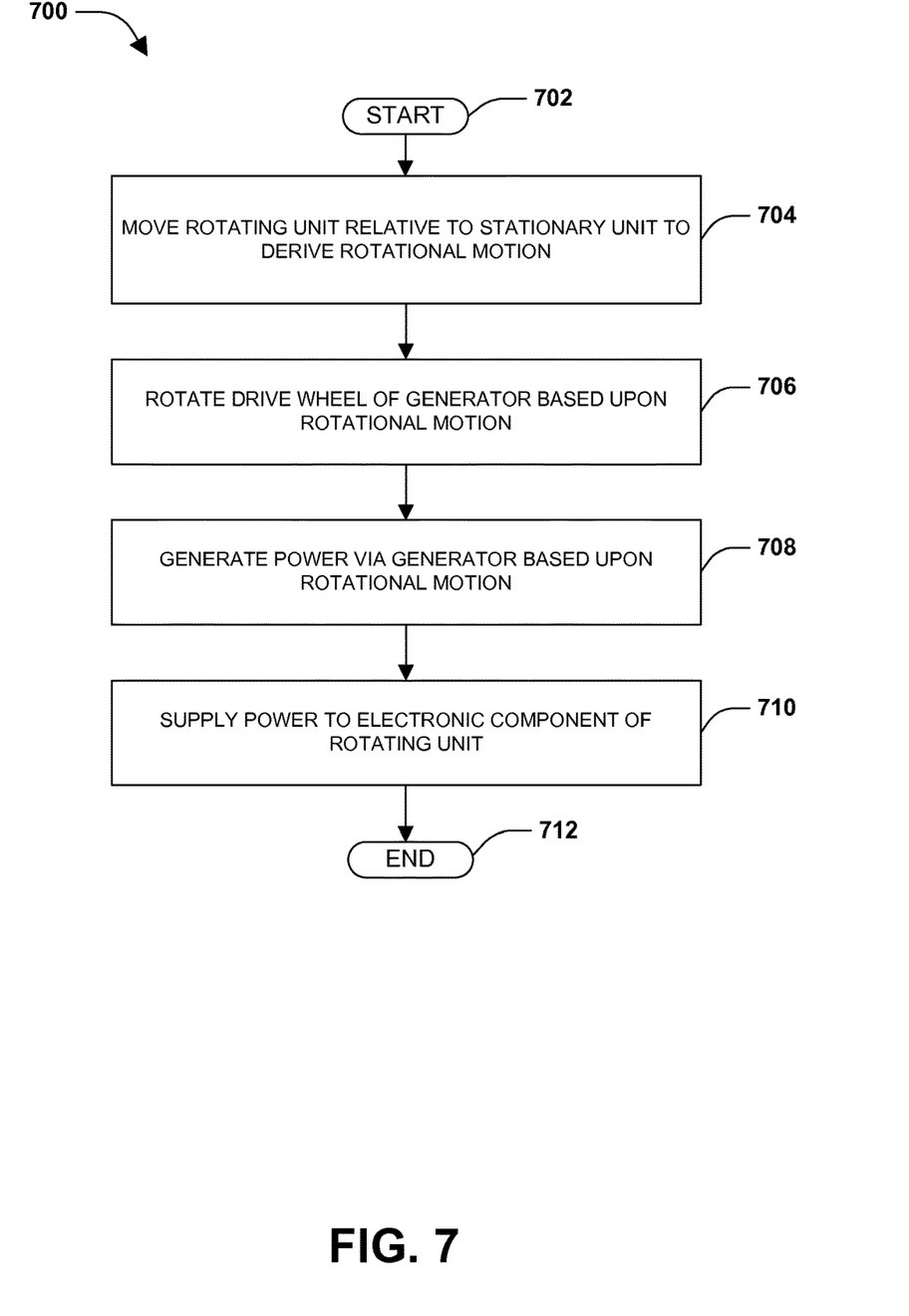
FIG. 7 is a flow diagram illustrating an example method for generating power in a radiation system.

Referring to FIG. 7, an example method 700 for generating power in a radiation system is provided. Such an example method 700 may be used to generate power within a rotating unit of the radiation system to be supplied to one or more electronic components of the rotating unit, for example.

The example method 700 starts at 702, and the rotating unit is moved (e.g., rotated) relative to a stationary unit of the radiation system to derive a rotational motion at 704. By way of example, the rotating unit may interface with a rotator of the stationary unit, which may rotate the rotating unit during an examination of an object, for example, causing a radiation source of the rotating unit to view the object from multiple angles. It may be appreciated that due to the rotating unit comprising the generator, the generator is typically moved or rotated in synchronization with the rotational motion of the rotating unit.

At 706 in the example method 700, a drive wheel of the generator is rotated along a drive mechanism of the stationary unit based upon the rotational motion of the rotating unit. That is, stated differently, as the rotating unit is rotated, a drive wheel of the generator moves along the drive mechanism (e.g., which may be fixed or may be rotated at a different speed and/or in a different direction than the rotating unit). The drive wheel is coupled to a shaft of the generator, and thus the shaft of the generator spins concurrently with the rotation of the drive wheel.

At 708 in the example method 700, power is generated via the generator based upon the rotational motion of the rotating unit. That is, stated differently, the rotational motion of the rotating unit causes the drive wheel to rotate, which in turn rotates a shaft of the generator. The rotation of the shaft creates an electrical field within the generator and/or causes power to be generated.

At 710 in the example method 700, the power is supplied to an electronic component of the rotating unit. The power may be directly or indirectly supplied to the electronic component from the generator. By way of example, in some embodiments, the electronic component is electrically coupled directly to the generator. In other embodiments, the electronic component is indirectly electrically coupled to the generator, where an intermediate electronic device, such as a switching component, power manipulation component, and/or an energy storage component may be situated between the electronic component and the generator.

In some embodiments, the electronic component is, at times, electrically decoupled from the generator. By way of example, a speed sensor may sense a speed of the rotational motion of the rotating gantry relative to the stationary unit and/or relative to a rotating guide of a drive mechanism of the stationary unit. When the speed sensor senses that the speed meets (e.g., meets and/or exceeds) a desired speed threshold (e.g., at which power having a desired frequency can be generated), a switching element may electrically couple the generator to the electronic component. When the speed sensor senses that the speed does not meet a desired speed threshold, the switching element may electrically decouple the generator from the electronic component, for example. As another example, an output sensor may sense a power characteristic of power output by the generator (e.g., voltage characteristic, frequency characteristic, or other power characteristic that is directly or indirectly a function of the speed of the rotating gantry, for example) and may trigger the switching element to electrically couple the generator to the electronic component when the power characteristic of the power meets a desired threshold. In some embodiments, such an output sensor may also be used to monitor performance (e.g., faults) of the generator.

Further, in some embodiments, when the speed sensor senses that the speed does not meet the desired speed threshold and/or detects the cessation of the rotational motion and/or when the output sensor senses that the power characteristic does not meet the desired threshold, the speed sensor and/or the output sensor may instruct an energy storage component or other auxiliary power supply to supply power to the electronic component, for example. By way of example, upon sensing that the speed does not meet the desired speed threshold, the speed sensor may issue a command that triggers a switching element to electrically couple the electronic component to a battery (e.g., of the rotating unit) and/or to electrically decouple the electronic component from the generator.

The example method 700 ends at 712.

Figure 8:
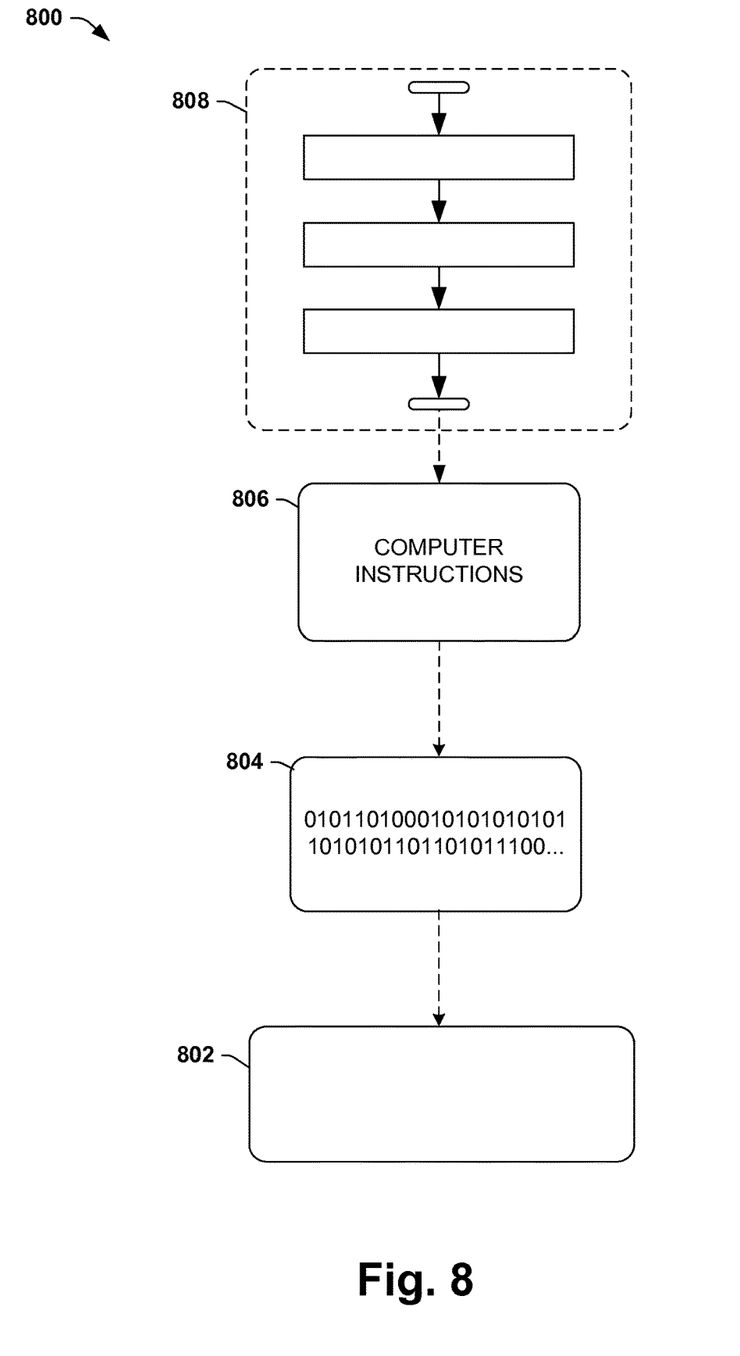
FIG. 8 is an illustration of an example computer-readable medium comprising processor-executable instructions configured to embody one or more of the provisions set forth herein.

Still an embodiment involves a computer-readable medium comprising processor-executable instructions configured to implement one or more of the techniques presented herein. An example computer-readable medium that may be devised in these ways is illustrated in FIG. 8, wherein the implementation 800 comprises a computer-readable medium 802 (e.g., a flash drive, CD-R, DVD-R, application-specific integrated circuit (ASIC), field-programmable gate array (FPGA), a platter of a hard disk drive, etc.), on which is encoded computer-readable data 804. This computer-readable data 804 in turn comprises a set of processor-executable instructions 806 configured to operate according to one or more of the principles set forth herein. In an embodiment 800, the processor-executable instructions 806 may be configured to perform an operation 808 when executed via a processing unit, such as at least some of the example method 700 of FIG. 7. In an embodiment, the processor-executable instructions 806 may be configured to implement a system, such as at least some of the example system 100 of FIG. 1 and/or at least some of the example power apparatus 500 of FIG. 5 and/or power apparatus 600 of FIG. 6. Many such computer-readable media may be devised by those of ordinary skill in the art that are configured to operate in accordance with one or more of the techniques presented herein. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Although the subject matter has been described in language specific to structural features or methodological acts, it is to be understood that the subject matter of the appended claims is not necessarily limited to the specific features or acts described above. Rather, the specific features and acts described above are disclosed as embodiment forms of implementing at least some of the claims.

Various operations of embodiments are provided herein. The order in which some or all of the operations are described should not be construed to imply that these operations are necessarily order dependent. Alternative ordering will be appreciated given the benefit of this description. Further, it will be understood that not all operations are necessarily present in each embodiment provided herein. Also, it will be understood that not all operations are necessary in some embodiments.

Moreover, "exemplary" is used herein to mean serving as an example, instance, illustration, etc., and not necessarily as advantageous. As used in this application, "or" is intended to mean an inclusive "or" rather than an exclusive "or." In addition, "a" and "an" as used in this application are generally be construed to mean "one or more" unless specified otherwise or clear from context to be directed to a singular form. Also, at least one of A and B and/or the like generally means A or B or both A and B. Furthermore, to the extent that "includes," "having," "has," "with," or variants thereof are used, such terms are intended to be inclusive in a manner similar to the term "comprising." The claimed subject matter may be implemented as a method, apparatus, or article of manufacture (e.g., as software, firmware, hardware, or any combination thereof).

As used in this application, the terms "component," "module," "system," "interface," and the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

Further, unless specified otherwise, "first," "second," and/or the like are not intended to imply a temporal aspect, a spatial aspect, an ordering, etc. Rather, such terms are merely used as identifiers, names, etc. for features, elements, items, etc. (e.g., "a first channel and a second channel" generally corresponds to "channel A and channel B" or two different (or identical) channels or the same channel).

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component that performs the specified function (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

What is claimed is:

1. A radiation system, comprising:
   a stationary unit; and
   a rotating unit configured for movement relative to the stationary unit, the rotating unit comprising:
      a radiation source configured to generate radiation; and
      a generator configured to generate power for an electronic component of the rotating unit,
         wherein the generator is configured to convert mechanical power to electrical power.

2. The radiation system of claim 1, wherein the generator is configured to generate power based upon the movement of the rotating unit relative to the stationary unit.

3. The radiation system of claim 1, wherein the electronic component comprises the radiation source.

4. The radiation system of claim 1, wherein the stationary unit comprises a drive mechanism along which a drive wheel of the generator is rotated based upon the movement of the rotating unit relative to the stationary unit.

5. The radiation system of claim 1, wherein the electronic component comprises a detector array.

6. The radiation system of claim 1, wherein the rotating unit comprises a load compensator configured to compensate for a change in a load placed on the generator by the electronic component.

7. The radiation system of claim 1, further comprising an auxiliary power supply configured to supply power to the electronic component.

8. The radiation system of claim 7, wherein the auxiliary power supply comprises an energy storage component.

9. The radiation system of claim 1, wherein the stationary unit comprises a drive mechanism configured to interface with a drive wheel of the generator, the drive mechanism comprising a guide configured for rotational motion.

10. The radiation system of claim 9, wherein the guide is configured to rotate relative to the rotating unit concurrently with motion of the rotating unit moving relative to the stationary unit.

11. The radiation system of claim 1, wherein the generator comprises a gear box configured to adjust a power characteristic of the power.

12. A method for generating power in a radiation system, comprising:
    moving a rotating unit of the radiation system relative to a stationary unit of the radiation system to derive a rotational motion;
    generating power at the rotating unit by converting rotational motion to electrical power; and
    supplying the power to an electronic component of the rotating unit.

13. The method of claim 12, wherein generating power comprises rotating a drive wheel of the generator along a drive mechanism of the stationary unit.

14. The method of claim 12, further comprising:
    sensing at least one of a speed of the rotational motion or a power characteristic of the power; and
    electrically coupling the generator to the electronic component when at least one of the speed meets a desired speed threshold or the power characteristic meets a desired threshold.

15. The method of claim 12, further comprising compensating for a change in load placed on the generator by the electronic component.

16. The method of claim 12, further comprising:
    detecting a cessation of the rotational motion; and
    supplying power to the electronic component via an auxiliary power supply responsive to the detecting.

17. The method of claim 12, further comprising moving the generator relative to the stationary unit in synchronization with the rotational motion.

18. The method of claim 12, further comprising adjusting a gear ratio of the generator to adjust a power characteristic of the power.

19. A radiation system, comprising:
    a stationary unit, comprising:
       a drive mechanism; and
    a rotating unit configured for rotational motion relative to the stationary unit, the rotating unit comprising:
       a radiation source configured to generate radiation;
       a detector array configured to detect at least some of the radiation; and
       a generator configured to generate power based upon the rotational motion, the generator comprising a drive wheel configured for rotation along the drive mechanism.

20. The radiation system of claim 19, wherein the drive mechanism comprises a guide configured to rotate relative to the rotating unit and the drive wheel configured to interface with the guide.

21. The radiation system of claim 1, wherein the generator is configured to use the movement of the rotating unit relative to the stationary unit to generate power.

* * * * *